United States Patent [19]
Huebner

[11] Patent Number: 6,120,505
[45] Date of Patent: *Sep. 19, 2000

[54] WIRE CLAMP ASSEMBLY

[75] Inventor: Randall J. Huebner, Aloha, Oreg.

[73] Assignee: Acumed, Inc., Beaverton, Oreg.

[ * ] Notice: This patent is subject to a terminal disclaimer.

[21] Appl. No.: 09/157,783

[22] Filed: Sep. 21, 1998

Related U.S. Application Data

[63] Continuation-in-part of application No. 08/457,624, Jun. 1, 1995.

[51] Int. Cl.⁷ ..................................................... A61B 17/56
[52] U.S. Cl. .............................. 606/74; 606/69; 606/103
[58] Field of Search .................................. 606/69, 70, 71, 606/72, 74, 75, 103; 24/129 W

[56] References Cited

U.S. PATENT DOCUMENTS

| | | |
|---|---|---|
| 76,141 | 3/1868 | Barnum . |
| 190,641 | 5/1877 | Stouffer . |
| 866,144 | 9/1907 | Kobert . |
| 2,171,524 | 9/1939 | Gates . |
| 2,276,571 | 3/1942 | Grypman . |
| 2,464,432 | 3/1949 | Brickman . |
| 2,986,787 | 1/1961 | Ackermann . |
| 3,641,629 | 2/1972 | Beardsley . |
| 3,754,303 | 8/1973 | Pollock . |
| 4,269,180 | 5/1981 | Dall et al. . |
| 4,473,925 | 10/1984 | Jansen . |
| 4,527,308 | 7/1985 | Tritton et al. . |
| 4,643,178 | 2/1987 | Nastari et al. . |
| 4,688,560 | 8/1987 | Schultz . |
| 4,790,303 | 12/1988 | Steffee . |
| 4,896,668 | 1/1990 | Popoff et al. . |
| 5,051,543 | 9/1991 | McGuire . |
| 5,190,545 | 3/1993 | Corsi et al. . |
| 5,312,410 | 5/1994 | Miller et al. . |
| 5,318,566 | 6/1994 | Miller . |
| 5,356,412 | 10/1994 | Golds et al. . |
| 5,415,658 | 5/1995 | Kilpela et al. ............................. 606/57 |
| 5,476,465 | 12/1995 | Preissman . |
| 5,649,927 | 7/1997 | Kilpela et al. . |
| 5,693,046 | 12/1997 | Songer et al. . |
| 5,702,399 | 12/1997 | Kilpela et al. . |
| 5,741,260 | 4/1998 | Songer et al. . |

*Primary Examiner*—Michael Buiz
*Assistant Examiner*—Julian W. Woo
*Attorney, Agent, or Firm*—Kolisch, Hartwell, Dickinson, McCormack & Heuser

[57] ABSTRACT

A wire locking sleeve and a wire. The sleeve has a bore and a deformation recess adjacent the bore. The sleeve around the bore is deformable toward the recess into a serpentine configuration for interlockingly engaging a portion of the wire disposed therein. Deformation of the sleeve around the bore is achieved by applying a transverse compressive force to the sleeve.

36 Claims, 4 Drawing Sheets

WIRE CLAMP ASSEMBLY

CROSS-REFERENCE TO RELATED APPLICATION

This application is a continuation-in-part of U.S. patent application Ser. No. 08/457,624, filed Jun. 1, 1995.

BACKGROUND OF THE INVENTION

The present invention relates to wire clamp assemblies and in particular, to a wire and sleeve assembly for securing together portions of a fractured bone to facilitate healing.

It is routine surgical practice to bind portions of a fractured bone together to ensure their proper alignment and to facilitate the knitting together of the bone portions. Wire and clamp assemblies are typically used for this purpose. Such assemblies can be subjected to very high tensile forces when, for example, the fractured bone is subjected to a high bending moment.

It is therefore important that the wire and clamp assembly embody the highest possible resistance to tensile forces which may cause such failures.

Known wire and clamp assemblies, as exemplified in FIG. 1, include a stranded, stainless steel cable and a sleeve having a pair of bores to receive the ends of the cable. Each cable end is clamped in one bore by urging the outer wall of the bore against the cable, squeezing the cable between the outer wall of the bore and the solid central portion of the sleeve. While such wire and clamp assemblies perform satisfactorily in most cases, they sometimes fail under high bending forces exerted on the fractured bone as described above. Moreover, the stranded stainless steel wire used in such assemblies is relatively expensive. A need therefore remains for a stronger, less expensive wire and clamp assembly for binding fractured bones.

SUMMARY OF THE INVENTION

The wire clamp of the present invention comprises a wire locking sleeve and a wire. The sleeve has a bore and a deformation recess adjacent the bore. The sleeve around the bore is deformable toward the recess into a serpentine configuration for interlockingly engaging a portion of the wire disposed therein. Deformation of the sleeve around the bore is achieved by applying a transverse compressive force to the sleeve.

The invention is also embodied in a method of securing a wire including the steps of providing a crimp block, the crimp block having a first wire-receiving bore formed therein and a deformation recess formed proximal to a region of the wire receiving bore, the first wire-receiving bore being slightly larger than the wire, inserting a portion of the wire into the wire-receiving bore and deforming a section of the wire proximal to the deformation recess, and the portion of the crimp block surrounding the section of the wire, toward the deformation recess to form a concavity in the wire and the wire-receiving bore.

DETAILED DESCRIPTION

Figure 4:
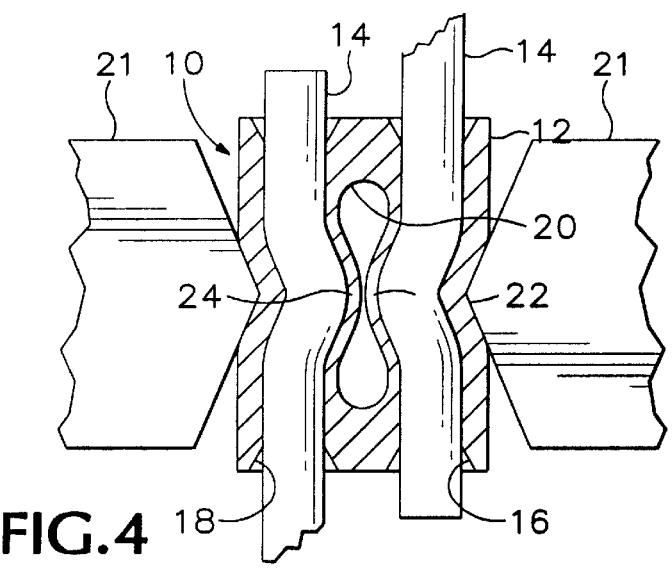
FIG. 4 is a cutaway plan view of a wire and clamp assembly shown in FIG. 3 wherein the longitudinal bores, longitudinal walls, and the wire ends have been deformed into interlocking serpentine configurations.
Figure 5:
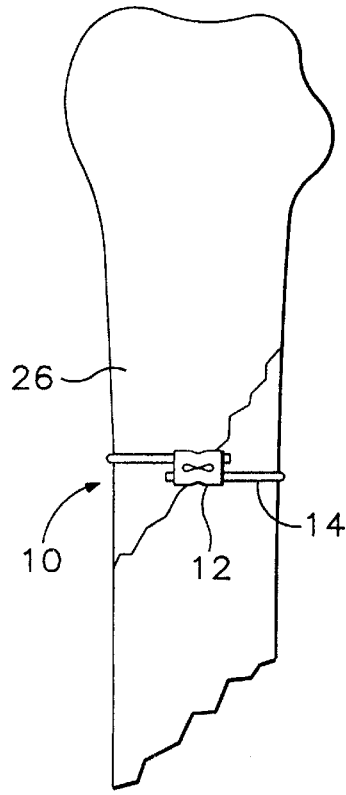
FIG. 5 is a top view of a wire and clamp assembly according to the present invention which has been applied to stabilize a fractured bone.
Figure 6:
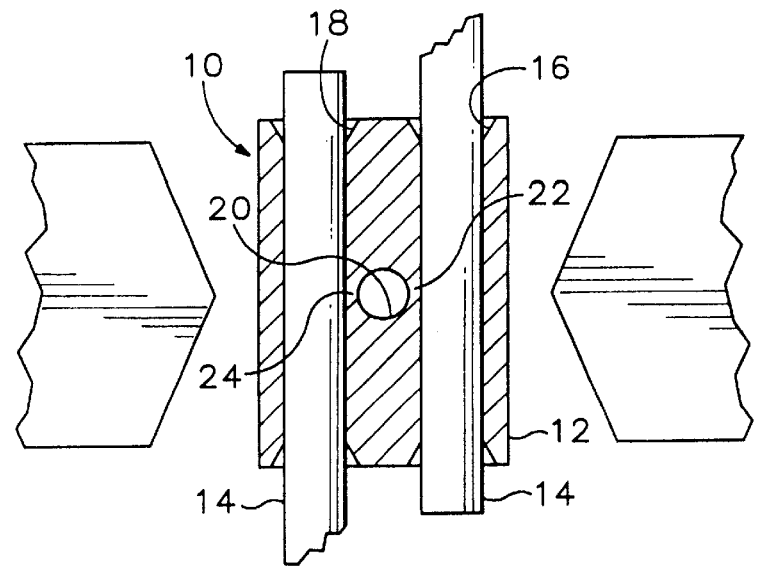
FIG. 6 is a cutaway plan view of an alternative embodiment of the wire clamp assembly having a circular opening.
Figure 7:
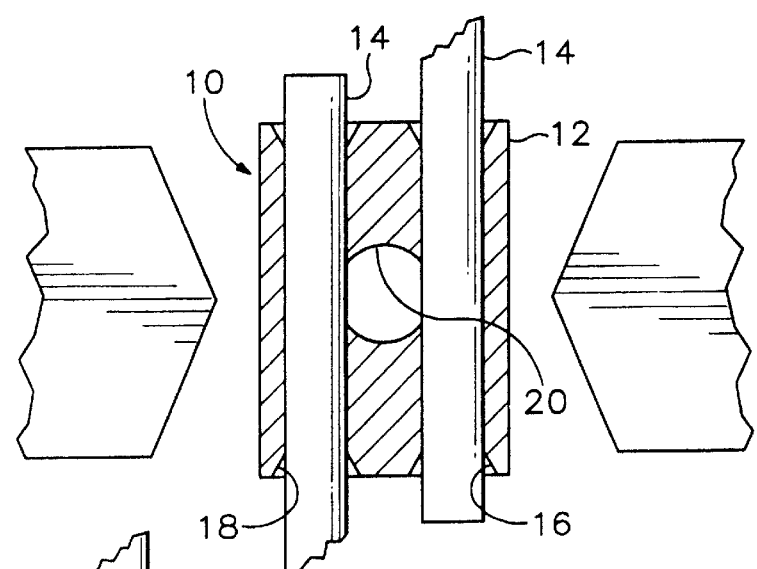
FIG. 7 is a cutaway plan view of an alternative embodiment of the wire clamp assembly where the circular opening communicates with the longitudinal bores.
Figures 8, 9, 10:
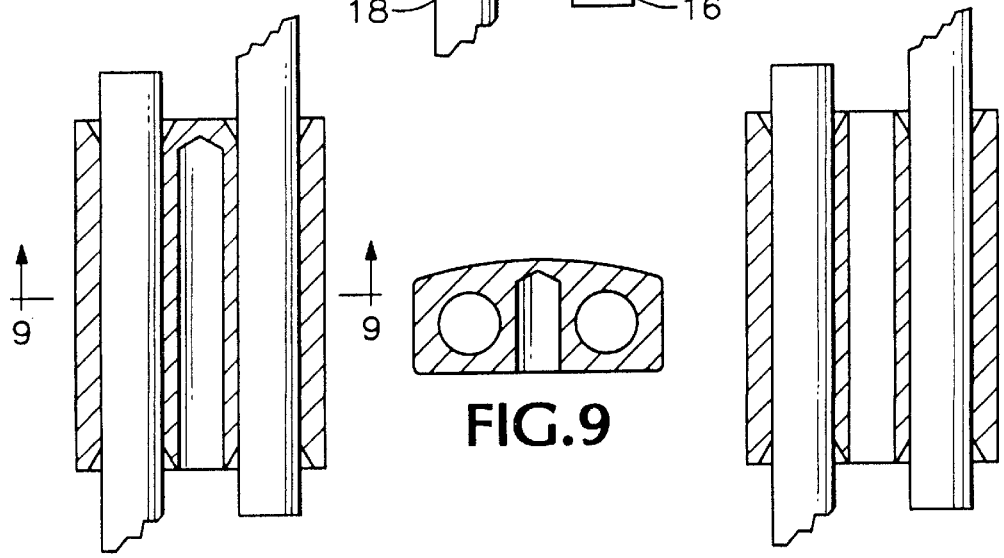
FIG. 8 is a cross-sectional view of an alternative embodiment of a sleeve according to the present invention.
FIG. 9 is a cross-sectional end view of the sleeve of FIG. 8, taken along line 9—9
FIG. 10 is a cross-sectional view of an alternative embodiment of a sleeve according to the present invention.
Figure 15:
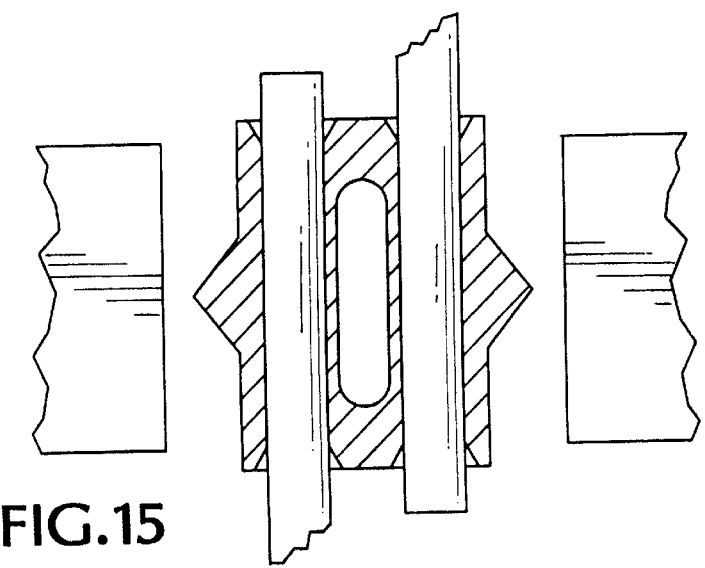
FIG. 15 is a cross-sectional view of an alternative embodiment of a sleeve according to the present invention.
Figure 16:
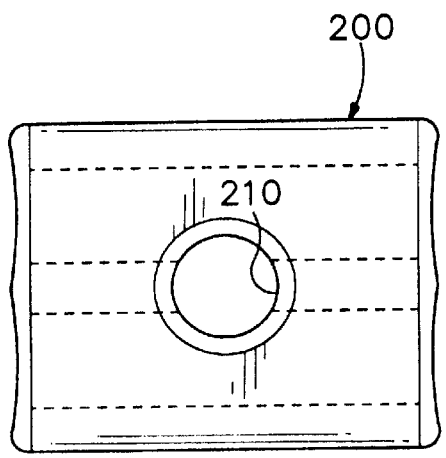
FIG. 16 is a top view of an alternative embodiment of a sleeve according to the present invention.
Figure 17:
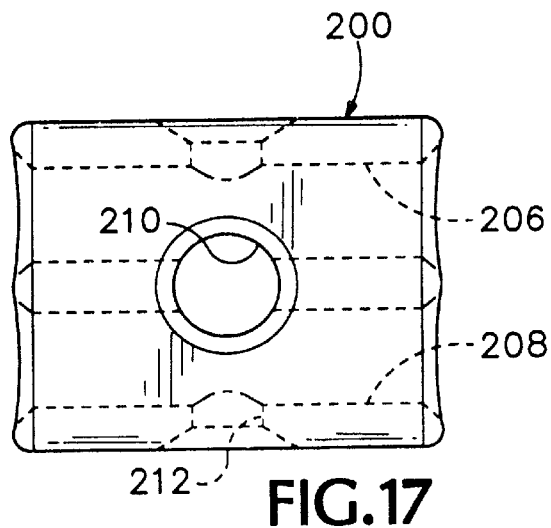
FIG. 17 is a bottom view of the sleeve of FIG. 16.
Figure 18:
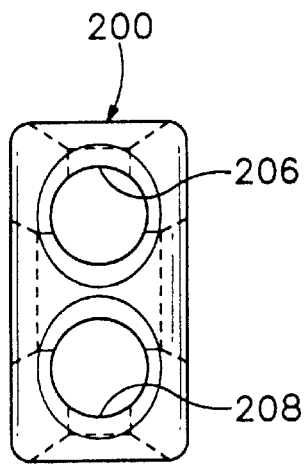
FIG. 18 is an end view of the sleeve of FIG. 16.
Figure 19:
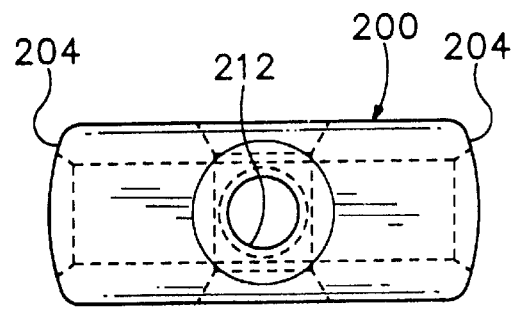
FIG. 19 is a side view of the sleeve of FIG. 16.

Referring now to FIGS. 2–7, a wire clamp 10 according to the present invention includes body 12 and wire 14. Body 12, also referred to as securing member 12, includes longitudinal bores 16 and 18, which preferably extend through the body. In alternative embodiments, either or both of longitudinal bores 16 and 18 may be blind bores which do not extend through body 12. Vertical opening 20, also referred to as deformation recess 20, extending through body 12 is preferably located between longitudinal bores 16 and 18, and is round as shown in FIGS. 6 and 7. In alternative embodiments, opening 20 may be shaped differently, including but not limited to the oblong shape shown in FIG. 3. FIG. 15 illustrates a variation of the sleeve of FIG. 3 in which ridges or bumps 30 are formed on the surface of the sleeve. This allows the sleeve to be deformed using a flat jawed tool or with a hammer. Opening 20 may extend only partially through body 12 and may be a blind hole, as shown in FIG. 8, or a blind channel, as shown in FIG. 9, or may be a thru-hole extending completely through to opposing sides of body 12, as shown in FIG. 10. In the embodiments shown in FIGS. 2–6, vertical opening 20 and longitudinal bores 16 and 18 together define walls 22 and 24 respectively. Wire 14 is a surgical grade wire, typically of stainless steel. In the preferred embodiment, wire 14 is monofilament for reasons described below, but may also be stranded.

Figure 1:
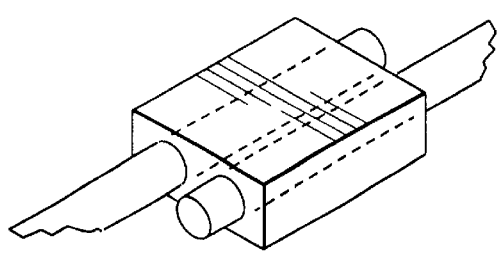
FIG. 1 is a perspective view of a prior art wire clamp assembly.
Figure 2:
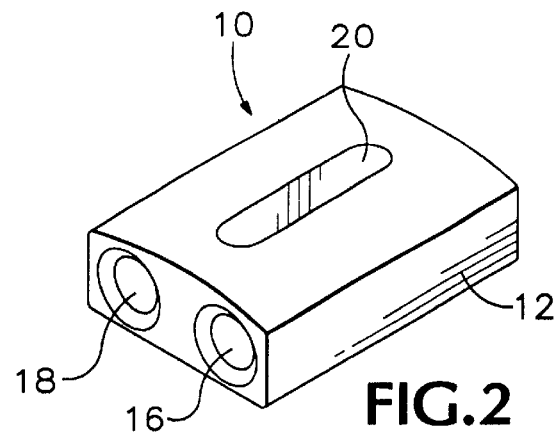
FIG. 2 is perspective view of one embodiment of a wire clamp sleeve according to the present invention.
Figure 3:
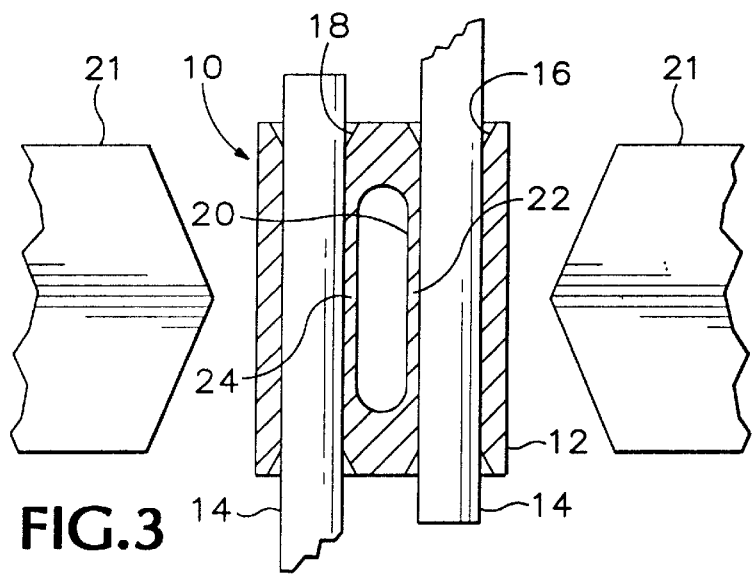
FIG. 3 is a cutaway plan view of the wire clamp of FIG. 2 having first and second ends of the wire inserted into the respective first and second longitudinal bores.

Wire clamp 10 is applied by passing wire 14 around fractured bone 26 in FIG. 5, inserting the wire ends into longitudinal bores 16 and 18, and then drawing them tight. (FIGS. 3, 5). Pliers 21 also referred to as crimping tool 21 having pointed jaws are then squeezed against body 12 to deform longitudinal bores 16 and 18 and the wire ends into interlocking, serpentine configurations (FIG. 4). Deformation of the body surrounding the longitudinal bores into a serpentine bore configuration is made possible by opening 20, which allows deformation of walls 22 and 24. The serpentine bore configuration achieved with the present invention provides greater clamping force than has heretofore been possible with prior art clamps in which only the outer wall of each longitudinal bore is urged against the stranded wire, but in which the inner wall of the bore is not deformable by any level of compressive force that can be readily applied in a surgical setting. Although the embodiments of the present invention are described in the context of a surgical application, it should be understood that the wire clamp of the present invention can be used wherever wire or cables must be secured.

Applicant has discovered that use of a monofilament, stainless steel surgical wire in conjunction with the serpentine configuration increases the strength of the wire clamp assembly even further. Increased strength is achieved by using a monofilament wire for at least two reasons. First, the stainless steel monofilament wire undergoes plastic deformation as it is deformed into its serpentine configuration. If the deformed monofilament wire is to be pulled from the body, sufficient force must be applied to rework the wire as it is passes through the serpentine bore. Reworking the wire is particularly difficult because the wire was work-hardened during its initial deformation. Also, there are three separate bends that must be reworked to slide the wire. Stranded wire on the other hand, is more resilient, and does not plastically deform or work-harden as much as monofilament wire when urged into the serpentine configuration achieved in the present invention. As a result, stranded wire can be separated from the body by a lesser force than that required for monofilament wire. Moreover, this greater strength achieved by use of monofilament wire is achieved at lower overall cost due to its lower cost compared to stranded stainless steel wire.

Figure 21:
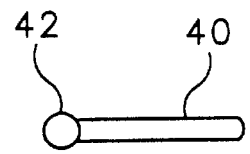
FIG. 21 shows a portion of a wire adapted for use in the present invention.

In an alternative embodiment (not shown), the clamp comprises body 12 and wire 14 having a first end permanently fixed in bore 16, and a second distal end. Body 12 has a longitudinal bore 18 to receive the distal end of wire 14. In use, the distal end of wire 14 is passed around the fractured bone and inserted into bore 18. Bore 18 and the second wire end are then deformed into an interlocking, serpentine configuration by use of a plier as described above. This embodiment provides the advantage of having only one portion of the wire which is slidable relative to the body, rendering installation easier in some instances. Alternatively, as shown in FIG. 21, a wire 40 with a beaded end 42 can be used to accomplish the same result. The bead catches on the end of the sleeve and prevents the wire from sliding out of the sleeve.

Figure 11:
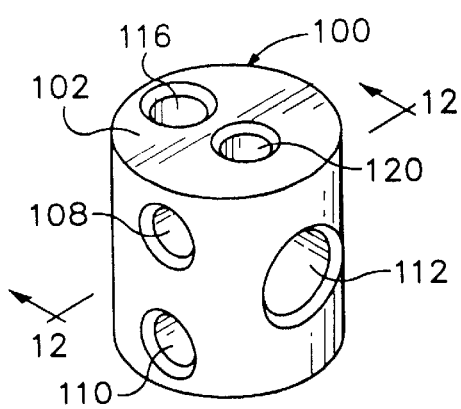
FIG. 11 is a perspective view of an alternative embodiment of a sleeve according to the present invention.
Figure 12:
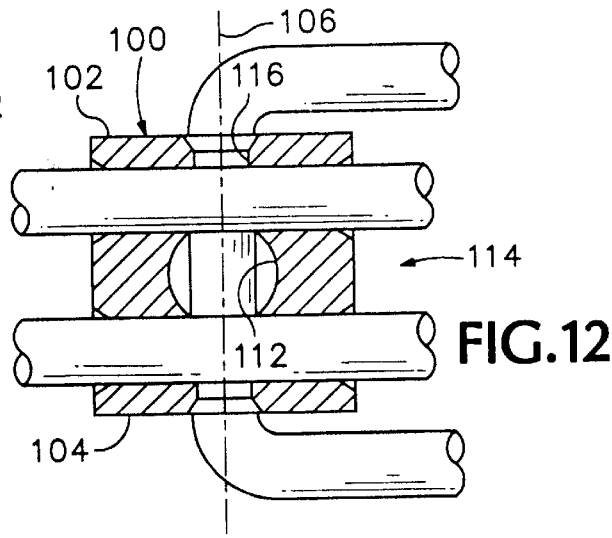
FIG. 12 is a cross-sectional view of the sleeve of FIG. 11, taken along line 12—12.
Figure 14:
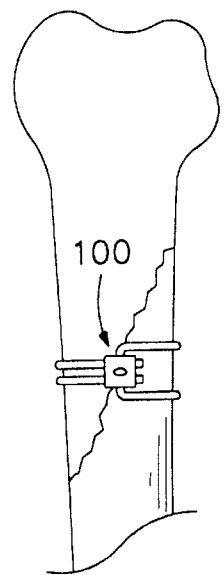
FIG. 14 shows the sleeve of FIG. 11 applied to repair a bone.
Figure 13:
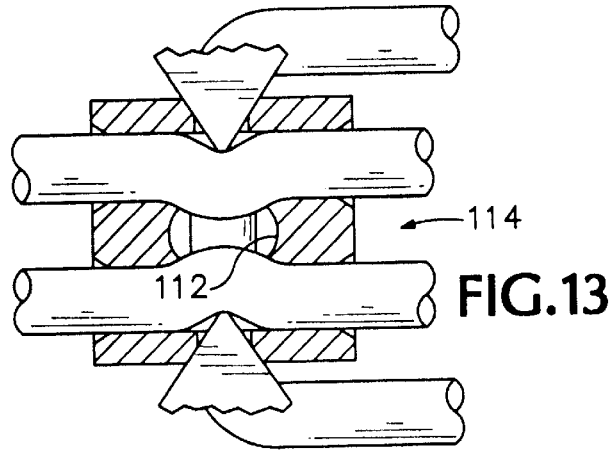
FIG. 13 is a cross-sectional view of the sleeve of FIG. 11, taken along line 12—12, after deformation.

Another embodiment of the present invention is shown in FIGS. 11–14. As shown in FIG. 11, the wire locking system of this embodiment includes a crimp sleeve 100. Crimp sleeve 100 is generally cylindrical with first and second ends 102, 104 extending transverse to a cylindrical axis 106. First and second wire-receiving bores 108, 110 extend through the sleeve in a direction transverse to the cylindrical axis. A deformation recess 112 extends through the sleeve in a direction transverse to the cylindrical axis as well as the axis of bores 108, 110. Recess 112 extends between the bores in a crimp zone 114 to provide room for the required locking deformation to occur. A crimp hole 116 is formed parallel to cylindrical axis 106, bisecting bores 108, 110. The crimp hole allows the pointed tips 118 of a crimping tool (not shown) to apply force directly to the sections of wire disposed in bores 108, 110, as shown in FIG. 13. A third wire receiving bore 120 is formed parallel to cylindrical axis 106 to receive a central portion of the wire therethrough, as shown in FIG. 14. In this configuration, the ends of the wire are received in bores 108, 110 to form a double-wire securing structure. While the various described embodiments involve securing the ends of a wire to form a loop, the invention can also be implemented with only one wire-receiving bore, as where only one end of a wire is to be anchored. In such cases the sleeve would typically be formed as part of, or attached to, some other structure.

Figure 20:
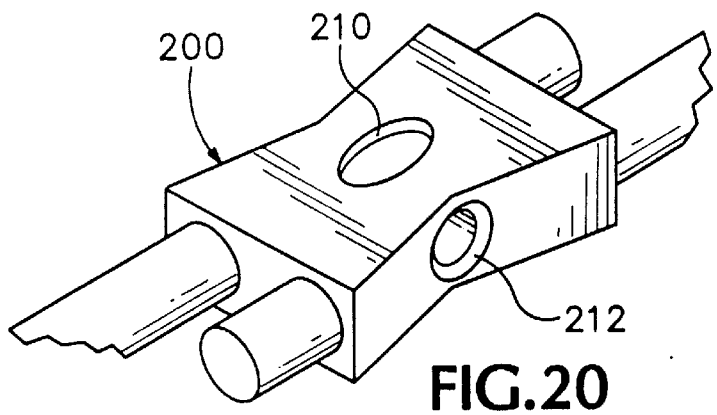
FIG. 20 is an isometric view of the sleeve of FIG. 16.

FIGS. 16–20 show a wire locking sleeve 200 according to one embodiment of the present invention. Sleeve 200 includes curved ends 202, 204 and first and second parallel, spaced-apart wire-receiving bores 206, 208 extending therebetween. A deformation recess 210 extends through the sleeve transverse to and between the wire-receiving bores. A crimp hole 212 transversely bisects the wire-receiving bores and the deformation recess to provide access for a crimping tool, as described above. When pressure is applied to the sides of the sleeve at the crimp hole ends, the sleeve is deformed inwardly toward the deformation recess, as shown in FIG. 20. Sleeve 200 is preferably formed from quarter-inch diameter round biocompatible stock, typically stainless steel or titanium. By virtue of the design and position of the holes, it is possible to manufacture the sleeve using only a screw machine.

One advantage of certain embodiments of the present invention is that they do not rely on deformation of the wire to achieve grip. This allows use of much harder wire, such as stainless steel or titanium, than can be used with sleeves rely on deforming the cross section of the wire to grip, as is the case with many sleeves designed for use with copper wire.

While the invention has been disclosed in its preferred form, the specific embodiments thereof as disclosed and illustrated herein are not to be considered in a limiting sense as numerous variations are possible. Applicants regard the subject matter of their invention to include all novel and non-obvious combinations and subcombinations of the various elements, features, functions and/or properties disclosed herein. No single feature, function, element or property of the disclosed embodiments is essential. The following claims define certain combinations and subcombinations which are regarded as novel and non-obvious. Other combinations and subcombinations of features, functions, elements and/or properties may be claimed through amendment of the present claims or presentation of new claims in this or a related application. Such claims, whether they are broader, narrower or equal in scope to the original claims, are also regarded as included within the subject matter of applicant's invention.

What is claimed is:

1. A system for securing a wire comprising a monolithic securing member having a first bore formed therein with a portion of the wire being disposed in the first bore and a second bore formed therein with a second portion of the wire being disposed in the second bore, the monolithic securing member further having a deformation recess disposed proximal to the first bore in a crimp zone, the wire and first bore being locally deformed transverse to a first elongate axis of the wire in a sinuous shape toward the deformation recess in the crimp zone to interlock the wire in the first bore.

2. The system of claim 1, wherein the deformation recess has an oblong shape.

3. The system of claim 2, wherein the deformation recess is centrally located in the securing member and extends more than half the length of the of the securing member.

4. The system of claim 1, wherein the deformation recess is a round opening, locally deformed in a region proximate the first bore.

5. The system of claim 1, wherein the deformation recess extends completely through the securing member to each of two opposing sides of the securing member.

6. The system of claim 1, wherein the securing member has at least two substantially parallel sides, each side being locally deformed in a respective region proximate the first bore.

7. The system of claim 1, wherein the securing member is a cylinder locally deformed in a region proximate the first bore.

8. The system of claim 1, wherein the wire is monofilament.

9. The system of claim 1, wherein the wire has a generally circular cross-section and the cross-section of the wire is relatively undisturbed in the crimp zone.

10. The system of claim 1, wherein the wire is stainless steel.

11. The system of claim 1, wherein the wire is work-hardened from being locally deformed.

12. The system of claim 1, the second portion of wire and second bore being locally deformed transverse to a second elongate axis of the wire in a sinuous shape toward the recess in the crimp zone to interlock the second portion of wire in the second bore.

13. The system of claim 12, wherein the deformation recess is located intermediate the first bore and the second bore.

14. The system of claim 12, wherein the first bore and the second bore are substantially parallel and each of the first bore and second bore is locally deformed towards the deformation recess.

15. The system of claim 12, wherein the securing member further includes a third bore for securing a central portion of the wire.

16. The system of claim 15, wherein the central portion of the wire is undeformed in the third bore.

17. The system of claim 15, wherein the third bore extends transverse to the first and second bore.

18. The system of claim 17, wherein the deformation extends through the securing member intermediate the first bore and the second bore, and bisects the third bore.

19. The system of claim 17, wherein the securing member is cylindrical and includes two opposing sides that are substantially parallel, each side being locally deformed in a respective region proximate the first bore or the second bore, and where the third bore extends between the two parallel opposing sides, and each of the first bore and the second bore extends between corresponding regions on a curved outer surface of the cylinder.

20. A system for securing a wire with a crimping tool, the system comprising:
a crimping sleeve including first and second wire-receiving bores extending at least partially into the crimping sleeve, a third wire-receiving bore extending through the crimping sleeve, and a deformation recess intermediate the first and second wire-receiving bores, the deformation recess being configured to at least partially collapse to facilitate deformation of the crimping sleeve; and
a wire including a central portion received by the third wire-receiving bore and a pair of end portions, each of the end portions being received by a respective one of the first and second wire-receiving bores;
wherein a portion of the crimping sleeve and the end portions of the wire received in the first and second wire-receiving bores each are configured to deform toward the deformation recess and interlock to secure the end portions in the crimping sleeve upon application of force to the crimping sleeve.

21. The system of claim 20 wherein the crimping sleeve further includes a crimp hole adjacent the first wire-receiving bore, the crimp hole being configured to receive a tip of a crimping tool, where a portion of the crimping sleeve is configured to deform into the deformation recess when force is applied through the crimping tool to the crimp hole.

22. The system of claim 21, wherein the crimp hole is a first crimp hole, and the crimping sleeve further includes a second crimp hole, located opposite the first crimp hole, and proximate the second wire-receiving bore, the second crimp hole being configured to receive a second tip of the crimping tool.

23. The system of claim 22, wherein the crimping sleeve is cylindrical.

24. The system of claim 23, wherein the third wire-receiving bore extends between two parallel surfaces of the cylinder.

25. The system of claim 24, wherein each of the first crimp hole and the second crimp hole is located on a respective one of the two parallel surfaces of the cylinder.

26. The system of claim 25, wherein each of the first wire-receiving bore and the second wire-receiving bore is located intermediate the first crimp hole and the second crimp hole, and extends through the sleeve in a direction transverse to a cylindrical axis of the crimping sleeve.

27. The system of claim 24, wherein the deformation recess extends through the crimping sleeve, transverse to the third wire-receiving bore and transverse to each of the first wire-receiving bore and the second wire-receiving bore.

28. The system of claim 21, wherein the first wire-receiving bore and second wire-receiving bore are located in parallel planes.

29. The system of claim 28, wherein the first wire-receiving bore and the second wire-receiving bore are parallel.

30. The system of claim 22, wherein each of the first wire-receiving bore and second wire-receiving bore is configured transverse to the third wire-receiving bore.

31. A device for securing a wire around a fractured bone with a jaw of a crimping tool, the device comprising:
a monolithic body including an outer surface, the body being formed of a bio-compatible material;
a first bore in the body, the first bore being configured to at least partially surround a first portion of the wire;
a second bore in the body, the second bore being configured to at least partially surround a second portion of the wire; and
an opening located proximate the first bore;
wherein, when the body is squeezed by the crimping tool, the opening is configured to at least partially collapse, a first portion of the body proximate the first bore is configured to deform into the opening, and the first bore is configured to form a concavity with the wire, thereby securing the wire within the first bore of the device.

32. The device of claim 31 further comprising:
a region of the outer surface defining a hole extending at least partially into the body, the hole being configured to receive a jaw of the crimping tool such that the crimping tool can deform the bore and the wire contained therein to secure the wire in the bore.

33. The device of claim 31, further comprising:
a region of the outer surface defining a hole that connects the outer surface to the bore and exposes the wire in the bore, the hole being configured to receive a jaw of the crimping tool such that the crimping tool can directly contact and deform the wire within the bore to secure the wire.

34. The device of claim 33, wherein a region of the body surrounding the first bore has a thickness of less than the diameter of the first bore.

35. The device of claim 33, wherein the opening extends at least across one-third the width of a top surface of the body.

36. The device of claim 33, wherein:
the bore is a first bore;
the portion of wire is a first portion of wire; and
the device further comprises a second bore spaced apart from the first bore, the second bore being configured to at least partially surround a second portion of wire;
wherein the opening lies intermediate the first bore and the second bore; and
wherein, upon deformation of the first portion of the body into the opening by the jaw of the crimping tool, a second portion of the body proximate the second bore is configured to deform into the opening and form a concavity with the second portion of wire, thereby securing the second portion of wire within the bore of the device.

* * * * *